United States Patent [19]

Gleisner

[11] Patent Number: 4,814,142

[45] Date of Patent: Mar. 21, 1989

[54] TEST STRIP HAVING A NON-PARTICULATE DIALYZED POLYMER LAYER

[75] Inventor: John M. Gleisner, Lynwood, Wash.

[73] Assignee: Polymer Technology International Corp., Issaquah, Wash.

[21] Appl. No.: 53,079

[22] Filed: May 22, 1987

[51] Int. Cl.⁴ .............................................. G01N 21/00
[52] U.S. Cl. ....................................... 422/56; 422/55; 422/57; 436/14; 436/169
[58] Field of Search ................................. 422/55–58; 436/169–170, 64

[56] References Cited

U.S. PATENT DOCUMENTS

| | | | |
|---|---|---|---|
| 3,802,842 | 4/1974 | Lange et al. | 23/253 |
| 3,942,995 | 3/1976 | Ichikawa et al. | 106/214 |
| 3,999,158 | 12/1976 | Rae | 337/360 |
| 4,042,335 | 8/1977 | Clement | 23/253 |
| 4,061,468 | 12/1977 | Lange et al. | 23/253 |
| 4,066,403 | 1/1978 | Bruschi | 23/230 |
| 4,110,079 | 8/1978 | Schaeffer et al. | 23/253 |
| 4,127,499 | 11/1978 | Chen et al. | 252/301 |
| 4,144,306 | 3/1979 | Figueras | 422/56 |
| 4,166,093 | 8/1979 | Smith-Lewis et al. | 422/56 |
| 4,258,001 | 3/1981 | Pierce et al. | 422/56 |
| 4,415,700 | 11/1983 | Batz et al. | 436/533 |
| 4,490,465 | 12/1984 | Limbach et al. | 435/14 |

Primary Examiner—Barry S. Richman
Assistant Examiner—Lyle Alfandary Alexander
Attorney, Agent, or Firm—George W. Neuner

[57] ABSTRACT

A diagnostic test strip for the detection of a analyte in a test fluid. The test strip has a reagent layer on a support layer. The reagent layer contains an analyte detection system in a non-particulate dialyzed latex polymer.

8 Claims, 1 Drawing Sheet

TEST STRIP HAVING A NON-PARTICULATE DIALYZED POLYMER LAYER

BACKGROUND OF THE INVENTION

The present invention relates to test strips useful for detecting components in a test sample, and particularly to stable test strips comprising a reagent layer containing a dialyzed polymer. Typically, the test strip used to test for the presence of a specific substance such as sugar in a liquid.

The analysis of test samples by use of test strips find utility in a variety of areas ranging from the medical field to food industries. Depending upon the reagent(s) present in the test strip, the strip can be used in detecting and diagnosing a variety of different conditions ranging, for example, from diabetes to pregnancy. In the food industry, the presence of, for example, maltose can be monitored in brewing where starch is converted to sugars such as maltose prior to fermentation to assure high yield from the grain starting materials.

Typically, test strips take advantage of a reaction between the substance to be tested and a reagent system present in the test strip. Generally, the test strip will take advantage of a color change or change in the wave length absorbed or reflected by the reagent system used as a result of this reaction. See, U.S. Pat. No. 3,802,842, U.S. Pat. No. 4,061,468 and U.S. Pat. No. 4,490,465. In testing for the presence of a substance such as sugar in a bodily fluid, test strips commonly take advantage of an oxidation/reduction reaction which occurs. The test strip is exposed to a drop of the fluid to be tested for a suitable period of time and there will be a color change if the sugar is present. Typically, the intensity of this change is proportional to the concentration of the sugar in the sample. The color of the test strip is than compared to a known standard which enables one to determine the amount of sugar present in the sample. This determination can be made by a visual check or by an instrument, such as using a light absorption or light transmission spectrophotometer for more accurate evaluation of concentration in the sample.

Because of the diagnostic applications, it is very important that the results obtained by these tests are reliable. Preferably, these strips will also have a long shelf life. One method for determining reliability and shelf life is by use of accelerated aging which comprises incubating the strip at an elevated temperature, e.g. 60° C., for a number of hours. We have now found that by constructing the strip by using a dialyzed latex polymer in the reagent layer, the resulting test strip maintains its integrity for a substantially longer time when exposed to elevated temperatures than a strip constructed using undialyzed polymer. Such elevated temperatures can be encountered during shipping or when stored in uncontrolled environments such as, for instance, the glove compartment of a car.

SUMMARY OF THE INVENTION

In accord with the present invention, a test strip is provided that comprises a support and a reagent layer wherein the reagent layer contains a dialyzed latex polymer and one or more reagents which react with a predetermined substance being detected. This test strip provides increased stability when stored at elevated temperatures. In one preferred embodiment of a test strip for detecting the presence of a sugar such as glucose, the reagent layer contains a dialyzed carboxylated vinyl acetate/ethylene copolymer and reagents including, for example, a charged polymer (e.g. sodium alginate, carboxymethyl cellulose), sodium azide, glucose oxidase, peroxidase, etc.) and an indicator that provides a color change when oxidized.

DETAILED DESCRIPTION OF THE INVENTION

Figure 1:
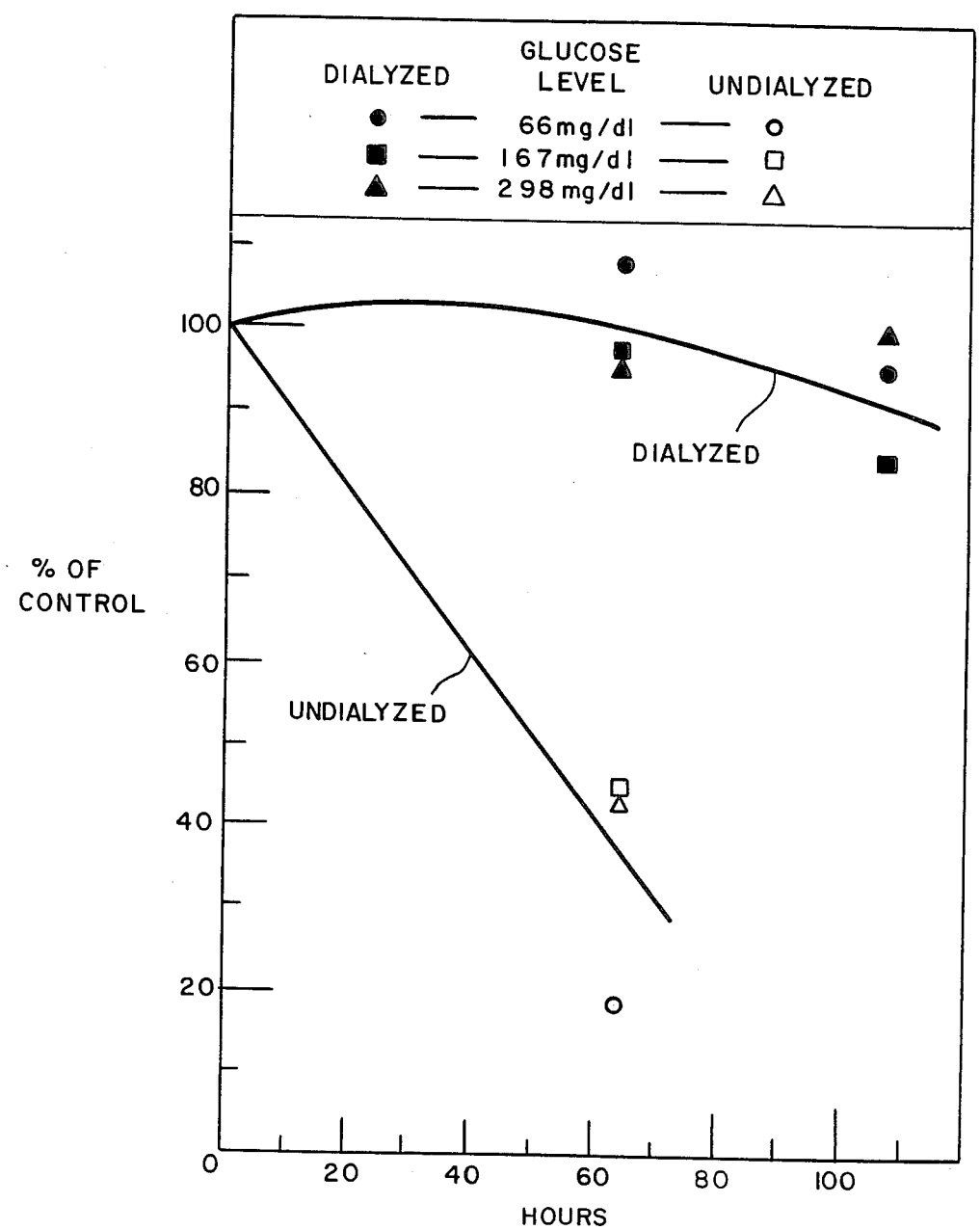
FIG. 1 is a chart comparing the reproducability of an "aged" dialyzed and an "aged" undialyzed strip as compared with unaged controls.

The dialyzed test strip of the present invention comprises a support having thereon a reagent layer. Preferably, this layer is essentially insoluble during the test and maintains structural integrity when exposed to the material to be tested.

Materials which can be used as such a support include glass fibers, plastics, hardened gelatin, various organic polymers such as polypropylene and the like. Preferably, the support is a solid non-absorbent material. In one preferred embodiment, the support has a matte finish on the side of the reagent layer. When the colorimetric change is read visually or by a reflective spectrophotometry, the support is preferably highly reflective to increase color contrast. Such a support includes the above materials as well as suitably finished metal foils. When the color change is read by transmission spectrophotometry, a transparent support is preferred.

The support is typically coated with a reagent layer which contains reagents to ascertain the presence of the substance sought to be detected in the liquid tested. In accord with the present invention, the reagent layer comprises a polymeric layer that contains a dialyzed latex polymer material and the reagent detection system. Such latex polymeric substances are well known in the art and include emulsions of polyvinyl compounds such as polyvinyl acetate, polyvinyl propionate, polyvinyl butyracetal, polyvinyl copolymers, and the like. Preferably, the material is a polyvinyl acetate-ethylene copolymer, although other latex emulsions well known to the skilled artisan can be used. The polymer is dialyzed by various techniques well known to the person of ordinary skill in the art. For example, a polyvinyl acetate/ethylene copolymer can be dialyzed by soaking the polymer in a sealed membrane tubing in water (preferably distilled or deionized) for a sufficient number of hours for removal of lower moledular weight materials to occur. Typically 60.80 hours is sufficient for a 100 gm batch. This membrane preferably has a molecular weight (MW) cut off of from about 10,000 to about 16,000 daltons, more preferably about 12,000 through 14,000 daltons. However, membranes having higher or lower MW cut offs can be used depending upon the particular emulsion being used. The dialysis removes unreacted monomers, lower molecular weight polymers and other contaminants. The use of a dialyzed latex polymer in the reagent layer results in a test strip which remains stable under exposure to elevated temperatures substantially longer than the corresponding test strip containing undialyzed latex polymer. See Table 1.

Although not wishing to be bound by theory, it is believed that over time the test strip having an undialyzed polymer layer undergoes a physical change wherein the layer which is relatively permeable to the liquid sample being tested becomes a layer which is substantially more impermeable to the liquid. In contrast, the dialyzed strip retains its permeability to the liquid substantially longer. Consequently, the accuracy and reliability of the undialyzed is diminished over time.

This dialyzed latex polymer preferably constitutes at least about 60% by weight of the dried reagent layer, more preferably at least about 75% by weight.

Test strips of the present invention can be made in any desired arrangement which optionally may include various additional layers. For example, it is possible to combine the reagent layer of the present invention optionally with various functional layers and membranes, as exemplified by the reagent layer, reflection layer, undercoating layer as disclosed in U.S. Pat. No. 3,999,158, radiation blocking layer as disclosed in U.S. Pat. No. 4,042,335 barrier layer as disclosed in U.S. Pat. No. 4,066,403, registration layer as disclosed in U.S. Pat. No. 4,144,306, migration inhibition layer as disclosed in U.S. Pat. No. 4,166,093 scintillation layer as disclosed in U.S. Pat. No. 4,127,499, scavenging layer as disclosed in Japanese Patent Publication No. 90859/1980 and destructive pod-like member as disclosed in U.S. Pat. No. 4,110,079, and the like, which are hereby incorporated by reference.

The methods of preparation of the aforesaid layers and the methods for incorporation of the aforesaid layers in test strips of the present invention may be the same as or similar to those as disclosed in said patents. In the aforesaid patents, there are also disclosed materials and methods useful in preparation of such optional layers.

The reagent layer of the present invention conveniently contains one or more reagent compositions to provide a reagent detection system for detecting a predetermined substance or component in a test sample. On interaction with the substance sought to be detected (analyte) or a reaction product or decomposition product of the analyte by the reagent detection system incorporated in the reagent layer, a detectable change is caused to occur. Preferably, the detectable change is a visible change such as for example, formation of a colored compound.

The expression "interaction" means chemical activity, catalytic activity (formation of enzyme-substrate conjugate formation), immunogenic activity (antigen-antibody reaction) and any other form of electrical, chemical or physical action.

Through these electrical, chemical or physical actions, it is possible to release, form or provide detectable changes within the test strip as is well known in the analytical field. By the aforesaid changes, there can be determined directly or indirectly the presence and/or concentration of the substance in the test sample.

The detectable change formed may preferably be detected by radiation measurement. The radiation measurement refers to a detection by use of an electromagnetic radiation measurement such as colorimetric measurement, fluorescence measurement, radiation counting, phosphorescense measurement and emission measurement.

Detectable components that can be used in the present invention, included dyes, pigments and complexes detectable by fluorescence measurement; emission tags; radioactive tags; chemical reagents; antigens; haptens; immunological species such as antibodies and antibody-antigen conjugates; enzymes; and precursors and reaction products of said components. The use of such components is well known to the person of ordinary skill in the art.

By using the appropriate reagent(s), e.g. the appropriate coupled enzymes, coupled antigens/antibody systems, etc., a wide variety of different substances can be tested for. These include sugars, proteins, acids, viruses, hormones, drugs and the like. The particular reagent system to be used depends upon the substance to be tested and many such systems for a wide variety of substances have been developed and are well known to the person of ordinary skill in the art.

For example, when testing for the presence of a sugar, such as glucose, the reagent layer typically contains a color indicator agent which, for example, detects the presence of hydrogen peroxide formed by the reaction of the sugar in the presence of a glucose oxidase and horseradish peroxidase. As a result of this reaction, the indicator agent e.g. a benzidine-type compound, changes color and the color change is proportional to the amount of sugar present. Other color indicator systems which can be used are well known to the person of ordinary skill in the art.

The amount of glucose present in the fluid is determined by comparing the results of the assay taken with known standards. For example, when the test strip is read visually, it is compared with a preprinted chart showing the color obtained when using glucose solutions of known concentration. Similarly, when the reading is by use of a spectrophotometer, the concentration is obtained from a standard graph prepared by using standard sugar solutions of known concentrations.

The following examples are provided to further illustrate how to make and use the present invention. Preferred embodiments are described and pertinent performance data is presented and illustrated. These examples are meant to be illustrative only and are in no way intended as limiting the scope of the invention described and claimed herein.

EXAMPLE 1

A glucose test strip was prepared as follows:

To a 50 ml tube the following was added in dry form:

(1) 100 mg 3-dimethyl amino benzoic acid (3-DMAB) (Sigma Chemical Co. D 1643)

(2) 13 mg 3-methyl-2-benzothiazolinone hydrazone (MBTH) (Sigma Chemical Co. M 8006)

(3) 100 mg citric acid monohydrate—sodium citrate dihydrate [when dissolved in water these buffer salts have a pH of 5.6]

(4) 50 mg of Loval ® 275 (PPG Industries, Inc.)

These dry materials were mixed with a spatula. Then 1.5 g of 10% water solution of carboxymethylcellulose (Sigma Chemical Co., C 8758) was added and mixed thoroughly with the above solids. Next was added 2.1 g of dialyzed carboxylated vinyl acetate ethyl copolymer latex. Again the materials were thoroughly mixed.

The latex copolymer was dialyzed by placing about 100 grams of carboxylated vinyl acetate/ethylene copolymer emulsion (Borden Co. W-138) into a membrane tubing with a molecular cut off of about 12,000–14,000 molecular weight fraction. The filled membrane was soaked in a water (distilled) bath at 20° C. for 60 hours to allow, for example, low molecular weight particles, unreacted monomer, catalyst, surfacant, etc. to pass through the membrane. During the 60 hours the water was continuously changed using an overflow system. The remaining dialyzed emulsion was then used in preparing the reagent layer.

Thereafter, 0.4 ml water, 0.03 ml of 25% aqueous solution of sodium lauryl sulfate (Sigma Chemical Co., L 5750), and 0.045 ml of 10M sodium hydroxide. The resultant mixture was mixed with a spatula. Then 0.18 ml of glucose oxidase (Sigma Chemical Co. G.8135) (10,000 U/ml saline) was pippetted to the tube as a liquid. Next 30 μl of peroxidase (Sigma Chemical Co. P-8375) (10,000 U/ml saline) was pippetted as a liquid to the tube. 10 μl of tartrazine (Sigma Chemical Co. T-0388) 7.5% in water was pippetted to the tube. The resulting mixture was mixed thoroughly with a spatula. This mixture was covered with plastic and allowed to stand for approximately 15 minutes.

A 10 mil polished-matte vinyl support purchased from North West Laminating Co., Seattle, Wash. prior to being coated with the above solution was cut to form cell rows and then wiped clean with methanol. The cell rows were 3"×21". The mixture was then pulled into a 10 ml syringe and ten approximately 6 mm drops were placed on each cell row. The solution was rough spread, then fine spread with a glass tube to result in the test strip having a wet coating about 4 mils thick, 0.5 cm wide, and 21 inches long.

The coated cell row was heated in an oven at 37° C. for 30 minutes followed by 45° C. for 2 hours. This process of coating and spreading the mixture was repeated for each cell row. The cell rows were then cut into strips of the desired size.

These strips were packaged with absorbent packs of silica gel and dried overnight at approximately 30° C. and 25 mm/Hg vacuum.

EXAMPLE 2

A drop of liquid containing glucose was than placed on a dry strip prepared as in Example 1 and wiped clean after one minute. A change in color was observed indicating the presence of glucose.

Glucose-containing samples having a known sugar content (66 mg/dl, 167 and 298) were than placed on the strips prepared as in Example 1, by the above procedure to obtain a standard color change for each concentration.

Thereafter, other strips prepared as in Example 1 were subjected to accelerated aging by heating the strip in an oven to a temperature of 60° C. for a period of either 63 hours or 110 hours. The three above glucose samples were used to test the "aged" strips by the above procedure and the results were compared with the unaged strips. The results are shown in Table 1.

TABLE 1

| | Dialyzed Test Strip | |
|---|---|---|
| Sugar Level | Concentration Determined By Test Strip | |
| concentration in test sample | Aged 63 hours at 60° C. (%)* | Aged 110 hours at 60° C. (%)* |
| 66 mg/dl | 97 | 91.3 |
| 167 mg/dl | 95 | 85.0 |
| 298 mg/dl | 109 | 101.3 |

*% Compared with Unheated Control (100%)

EXAMPLE 3

Test strips prepared by the same methods as described in Example 1, except that they were not dialyzed, the amount of MBTH was increased to 30 mg (dialysis removes materials which react with MBTH) and the amount of 10M sodium hydroxide was increased to 0.070 ml (dialysis also reduced the acidity of the latex), were also subjected to accelerated heating at 60° C. for 63 hours. These "aged" strips were then tested using drops of the three known above described glucose solutions as described in Example 2. These samples were similarly compared with unaged counterparts as described in Example 2 with the results indicated in Table 2.

A comparison of these results (See FIG. 1) demonstrates that the test strip of the present invention is more stable and provides much more reliable results when exposed to elevated temperatures, even under accelerated aging conditions, whereas the undialyzed strips do not.

TABLE 2

| | Undialyzed Test Strip |
|---|---|
| Sugar Level Concentration in Test Sample | Concentration Determined By Test Strip Aged 63 hours at 60° C. (%)* |
| 66 mg/dl | 19.7 |
| 167 mg/dl | 45.2 |
| 298 mg/dl | 44.6 |

*% Compared with Unheated Control (100%)

This invention has been described in detail, including preferred embodiments thereof. However, it will be appreciated that those skilled in the art, upon consideration of this disclosure, may make modifications or improvements without departing from the spirit and scope of the invention as set forth in the claims.

We claim:

1. A diagnostic test strip for the detection of a predetermined substance in a fluid wherein the strip comprises a support having thereon a reagent layer wherein the reagent layer contains a non-particulate dialyzed latex polymer and dispersed therein a reagent detection system consisting essentially of one or more reagent compositions which react with the substance to provide a detectable change, wherein the dialyzed latex polymer constitutes at least about 60% by weight of the dry reagent layer.

2. The tests strip of claim 1 wherein the dialyzed latex polymers comprises a carboxylated polyvinyl acetate-/ethylene copolymer.

3. The test strip of claim 1 wherein the dialyzed latex polymer constitutes at least about 75% by weight of the reagent layer.

4. The test strip of claim 1 wherein the dialyzed latex polymer comprises a carboxylated polyvinyl acetate-/ethylene copolymer.

5. The test strip of claim 4 wherein the reagent layer contains a reagent detection system for detecting glucose.

6. The test strip of claim 5 which provides a visible change when glucose is present.

7. The test strip of claim 6 wherein the visible change is a change of color.

8. A diagnostic test strip comprising a transparent support having thereon a reagent layer comprising dialyzed non-particulate carboxylated vinylacetate/ethylene copolymer and dispersed therein a reagent detection system consisting essentially of glucose oxidase, peroxidase, and a color indicator that changes color when exposed to glucose, wherein the dialyzed latex copolymer constitutes at least about 60% by weight of the dry reagent layer.

* * * * *